United States Patent [19]

Prengel

[11] Patent Number: 5,354,374
[45] Date of Patent: Oct. 11, 1994

[54] IRON OXIDE PIGMENTS

[75] Inventor: Constanze Prengel, Nienw-Vennep, Netherlands

[73] Assignee: Merck Patent Gesellschaft mit beschrankter Haftung, Darmstadt, Fed. Rep. of Germany

[21] Appl. No.: 975,340

[22] Filed: Nov. 16, 1992

[30] Foreign Application Priority Data

Nov. 16, 1991 [DE] Fed. Rep. of Germany ....... 4137764

[51] Int. Cl.$^5$ ............................................... C09C 1/22
[52] U.S. Cl. ................................... 106/459; 106/439; 106/450; 106/456
[58] Field of Search ............... 106/436, 439, 450, 456, 106/457, 481, 459

[56] References Cited

U.S. PATENT DOCUMENTS

| | | | |
|---|---|---|---|
| 3,036,889 | 5/1962 | Frey | 106/456 |
| 3,836,378 | 9/1974 | Hahnkamm et al. | 106/456 |
| 4,053,325 | 10/1977 | Vanderheiden | 106/456 |
| 4,567,030 | 1/1986 | Yuasa et al. | 106/481 |
| 4,631,089 | 12/1986 | Rademachers et al. | 106/456 |
| 4,675,251 | 6/1987 | Matijevic et al. | 427/215 |
| 4,775,520 | 10/1988 | Unger et al. | 423/335 |
| 4,867,793 | 9/1989 | Franz et al. | 106/456 |
| 4,911,903 | 3/1990 | Unger et al. | 423/335 |

*Primary Examiner*—Karl Group
*Assistant Examiner*—Chris Gallo
*Attorney, Agent, or Firm*—Millen, White, Zelano & Branigan

[57] ABSTRACT

The invention relates to iron oxide pigments based on silica, zirconium dioxide and/or titanium dioxide particles coated with iron oxide, the iron oxide content being more than 350% by weight, relative to the weight of the silica, zirconium dioxide and/or titanium dioxide particles.

16 Claims, No Drawings

IRON OXIDE PIGMENTS

BACKGROUND OF THE INVENTION

The invention relates to iron oxide pigments based on silica, titanium dioxide and/or zirconium oxide particles coated with iron oxide.

Pigments of this type which are based on monodisperse, spherical titanium dioxide particles are described in EP 0,192,485, corresponding to U.S. Pat. No. 4,675,251; these spherical titanium dioxide substrates preferably have a diameter in the submicron range of between 0.2 and 0.8 $\mu$m and the iron oxide layer in particular has a thickness of between 10 and 300 Å, which corresponds to a weight proportion of not more than about 60% by weight, relative to the weight of the titanium dioxide substrate. If the iron oxide coating is present as an $\alpha$- or $\gamma$-$Fe_2O_3$ modification, orange-red to red-brown pigments are obtained; if an $Fe_2O_3$-coated pigment is subjected at elevated temperatures of, for example, more than 400° C. to a reducing gas atmosphere, a grey-black to black pigment which has magnetic properties and a magnetite coating is obtained. The pigments described in EP 0,192,485 have a high covering power and a high color strength.

However, the disadvantage of $Fe_2O_3$-coated pigments is that they have a very narrow color spectrum and are virtually limited to orange-red–red-brown hues; black pigments can only be obtained by conversion of the $Fe_2O_3$ coating into a magnetite coating, which gives the pigments, at the same time, ferromagnetic properties, which is, however, undesirable in many applications.

SUMMARY OF THE INVENTION

One object of the present invention was to provide iron oxide pigments which have good covering power and high color strength and cover a broader color spectrum and in particular other red hues than the pigments described in EP 0,192,485. A further object was to provide a black, non-magnetic iron oxide. Further objects of the present invention are obvious to one skilled in the art from the description below.

It has been found that this object can be achieved by providing the pigments according to the invention.

Accordingly, the invention relates to iron oxide pigments based on silica, titanium dioxide and/or zirconium oxide particles coated with iron oxide, the iron oxide content being more than 350% by weight, relative to the weight of the silica, titanium dioxide and/or zirconium oxide particles.

The invention further relates to a process for the preparation of the pigments according to the invention and the use of these pigments in formulations such as paints, plastics and cosmetics.

It has been found that pigments having excellent properties can be obtained by depositing very thick iron oxide layers on the silica, titanium dioxide and/or zirconium dioxide particles. Despite the high weight proportion of at least, and preferably, more than 350% by weight, in particular more than 500% by weight and very particularly more than 750% by weight, in each case relative to the weight of the titanium dioxide, zirconium dioxide and/or silica substrate, a strongly adhering, compact iron oxide layer forms around the substrate particles. The pigment is very stable, and the iron oxide cover has no tendency to peel off from the substrate particles. Microscopic viewing of the pigments shows that the iron oxide layer has no tendency to cracking even at very high weight proportions of more than 1000 or even more than 1500% by weight and is smooth and compact.

Suitable substrates are small $SiO_2$, $TiO_2$ and/or $ZrO_2$ particles which have an irregular 3-dimensional shape and can in particular be more or less spherical. The particle diameter is preferably in the submicron range of between 0.08 and 0.9 $\mu$m and in particular between 0.1 and 0.75 $\mu$m. However, larger substrate particles having diameters of up to 5 $\mu$m are also suitable, although substrates having diameters of more than 2.5 $\mu$m are in general less preferred.

The substrate particles are 3-dimensional, non-platelet-like particles, i.e. the ratio of the average expansion in the two main dimensions to the expansion in the third dimension is preferably not greater than 3 and in particular not greater than 2. The use of more or less spherical particles is preferred, since in this case the iron oxide layer can grow uniformly, leading to particularly stable pigments.

If substrate particles having a very broad distribution of their diameter around the average diameter are used, the coated particles have in some cases iron oxide layers of significantly different thickness, which may impair the color purity of the product.

Well-defined products of good color purity are obtained by using spherical, monodisperse substrates, monodisperse substrates being understood to mean those having a narrow distribution of their diameter around the average diameter; their standard deviation is preferably not more than 20% and in particular less than 10%. Monodisperse $SiO_2$ can be prepared, for example, according to DE 35 34 143 or DE 36 16 133, corresponding to U.S. Pat. Nos. 4,775,520 and 4,911,903, and the preparation of spherical, monodisperse titanium dioxide particles is described in U.S. Pat. No. 4,241,042. Monodisperse $SiO_2$, $TiO_2$ and $ZrO_2$ is also commercially available (for example monodisperse $TiO_2$ under the name P112F from Instituto Guido Domegamii, Novara, Italy or monodisperse $SiO_2$, tradename Monospher TM, from E. Merck, Darmstadt). Monodisperse $TiO_2$ is commercially available not only in the anatase but also in the rutile modification.

It is possible to use either only $TiO_2$, $SiO_2$ or $ZrO_2$ particles or, alternatively, it is also possible to use mixtures of different particles.

The pigments according to the invention are prepared by suspending the $TiO_2$, $SiO_2$ and/or $ZrO_2$ substrate particles in an aqueous solution and bringing the pH to a value favorable for the precipitation of the iron oxides, the selected value being in general between 3 and 6 and in particular between 3 and 5. The pH is selected such that the iron oxide layer is deposited directly on the substrate particles and no secondary precipitations take place in the suspension. An aqueous solution of one or more iron salts is then metered in, while maintaining the pH of the suspension substantially constant by simultaneous addition of a base.

It is possible to add iron(III) compounds, such as, for example, iron(III) halides, such as, for example, iron(III) chloride or iron(III) sulfate and also iron(II) compounds, such as, for example, ammonium iron(II) sulfate, iron(II) halides and in particular iron(II) sulfate.

When iron(III) compounds are used, $\alpha$-$Fe_2O_3$ or $\alpha$-iron(III) oxide hydrate is precipitated. By precipitating iron(II) compounds in the presence of an oxidizing agent, such as, for example, atmospheric oxygen, a nitrate, such as ammonium nitrate, sodium nitrate or potassium nitrate or even a chlorate, it is possible to produce defined $\alpha$-, $\beta$- or $\gamma$-FeOOH layers, magnetite layers, $\alpha$-Fe$_2$O$_3$ and $\gamma$-Fe$_2$O$_3$ layers, as described in U.S. Pat. No. 3,926,659 for the deposition of iron oxide layers on platelet-like mica substrates; the process described there can also be used directly for the coating of the non-platelet-like substrates used according to the invention. Preferably, the processes described in U.S. Pat. No. 3,926,659 are modified according to EP 0,246,523 such that the oxidizing agent is not initially introduced into the suspension but is metered in together with the iron(II) salt solution. This measure also produces significantly smoother and more compact iron oxide layers than in the process according to U.S. Pat. No. 3,926,659 in the preparation of the pigments according to the invention based on non-platelet-like substrates (EP 0,246,523 relates to the coating of platelet-like substrates).

After deposition is complete, the coated substrates are separated off, and, if desired, washed, dried and, if desired, ignited. It is possible to produce the iron oxide hydrate or iron oxide layers mentioned, iron(III) oxide layers being preferred. Particular preference is in general given to pigments according to the invention having a paramagnetic $\alpha$-Fe$_2$O$_3$ layer, since the ferromagnetic properties of $\gamma$-Fe$_2$O$_3$ are undesirable in many applications; as is known, $\gamma$-Fe$_2$O$_3$ is converted upon ignition in air at temperatures of more than about 400° C. into $\alpha$-Fe$_2$O$_3$.

When an iron(III) oxide or iron(III) oxide hydrate layer is precipitated, the increase in thickness of the iron(III) oxide layer can be monitored via the color. Thus, iron(III) oxide weight proportions of between about 20 and 150% by weight produce orange-red to red-brown hues, while wine red- red-violet hues are obtained at the lower end of the weight range according to the invention which change to hues of eggplant color and grey-red and finally from dark violet to black at high weight proportions of 1000–2000% by weight. The weight proportion of Fe$_2$O$_3$ applied in each case can thus be easily detected by the color and the coating process can be stopped when the desired hue has been reached.

After being separated off and, if desired, washed, the pigments obtained are dried and then usually ignited at temperatures of more than 600° C.; at ignition temperatures of more than 850° C. and in particular 900° C. or more, a color shift of the pigments to darker hues is observed in many cases (see Example 4). There is little tendency to agglomeration, and the pigment is formed in virtually all instances as a dry, easily handleable powder. However, if agglomerate should form to a troublesome extent, the ignited pigment can, if desired, be milled under mild conditions (e.g. under water in a ball mill), mostly destroying the aggregates but leaving the pigments according to the invention substantially intact.

The pigments according to the invention are distinguished by strong shades which satisfy even the highest aesthetic requirements and by a high covering power. Particular preference is given to pigments according to the invention having a high $\alpha$-Fe$_2$O$_3$ coating, showing grey-red-black hues and being nonmagnetic.

Moreover, the pigments according to the invention, when applied as a drawdown, have a color flop, which is surprising, since the pigments according to the invention are not based on platelet-like substrates; however, the color flop is often not very strong, but becomes more distinct the higher the iron oxide content. The color flop to be achieved can be increased considerably by incorporating the pigments according to the invention together with luster-producing platelet-like pigments in paint formulations; these platelet-like pigments can be transparent or semitransparent substrates coated with metal oxide layers, such as, for example, mica (pearl luster pigments) or, alternatively, small metal platelets (for example Al platelets which, if desired, are covered by polymers). The ratio of the amount of the pigments according to the invention and the amount of the luster-producing platelet-like pigments is preferably between 0.1 and 10 and in particular between 0.5 and 5; the weight proportion of the luster-producing platelet-like pigments in paint formulations of this type is preferably between 1 and 20% by weight.

Furthermore, it has been found that a further additional, very interesting color effect can be observed by doping the iron oxide layer with one or more metal oxides selected from a group of metal oxides comprising SnO$_2$, Al$_2$O$_3$, In$_2$O$_3$, ZrO$_2$, B$_2$O$_3$, MgO, BaO, CaO, SiO$_2$, NiO and TiO$_2$: the pigments according to the invention containing such a doped iron oxide layer continue to have, on the one hand, a very strong color which, however, is in some cases a little lighter compared with an undoped pigment having the same iron oxide weight proportion; on the other hand, the doped pigments show a certain transparency and a covering power which is reduced compared with undoped pigments, which is of great interest for many applications and can result, say, in aesthetically highly attractive coatings.

A particularly preferred doping component comprises a smaller group of colorless metal oxides made up of SnO$_2$, Al$_2$O$_3$, In$_2$O$_3$, ZrO$_2$, B$_2$O$_3$, MgO, BaO, CaO, SiO$_2$ and TiO$_2$.

The doped iron oxide layer is produced by adding an aqueous solution containing one or more iron salts and one or more doping salts at a pH suitable for the precipitation of the doped iron oxide layer; it is of course also possible to add iron salts and doping salts separately. The pH selected is such that the doped iron oxide layer is deposited directly on the substrate particles and no secondary precipitations take place in the suspension.

If the iron oxide deposition and the deposition of the doping salt cannot take place simultaneously at a specific pH due to a large difference in the deposition rates, it is also possible to stop deposition of the iron oxide, for example after about ¼ of the entire iron oxide amount has been applied by stopping the addition of the iron salt, in order to be able to bring the pH to a value favorable for precipitation of the doping salt. At this pH, a portion of the doping salt is then applied and the pH is subsequently again brought to the pH favorable for the iron oxide deposition; this procedure is then repeated three more times in the example mentioned. The change in the pH is effected by metering in acids and bases. Coprecipitation carried out in one step is preferred, since it is a considerably less complicated procedure.

A person skilled in the art can select suitable doping salts without problems from standard textbooks of inorganic chemistry, such as, for example, Hollemann-Wiberg, Lehrbuch der anorganischen Chemie (Textbook of Inorganic Chemistry), Berlin 1976 and also establish suitable deposition conditions. The deposition of various metal oxides on platelet-like substrates is described, for example, in U.S. Pat. No. 3,087,828, U.S.

Pat. No. 3,087,829, DE 19 59 998, DE 20 09 566, DE 22 14 545, DE 22 44 298, DE 23 13 331, DE 25 22 572, DE 31 37 808, DE 31 37 809, DE 31 51 343, DE 31 51 354, DE 31 51 355, DE 32 11 602 and DE 32 35 017 and it was found that the deposition conditions described there can also be used for the coating of the 3-dimensional substrates of the present invention.

The weight of the doping component(s) is preferably between 0.5 and 30% and in particular between 1 and 15%, relative to the iron oxide weight. Aesthetically particularly attractive pigments are obtained at doping levels of between 1 and 10%. It is possible to use up to 5 different doping salts, although the use of not more than 2 doping salts is preferred.

The pigments according to the invention are distinguished by strong colors and a high covering power, it being possible to reduce the latter by doping the iron oxide layer selectively with a view to the intended use of the pigment. Using the pigments according to the invention, an entire range of various red hues down to black hues is available, a particular achievement being the preparation of a black non-magnetic iron oxide pigment. The pigments according to the invention are aesthetically very attractive and extend the range of available pigments into very interesting hues. Accordingly, the pigments according to the invention have significant economic importance.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

The entire disclosure of all applications, patents and publications, cited above, and of corresponding German application P 41 37 7648, and hereby incorporated by reference.

EXAMPLES

Example 1

5 g of monodisperse $TiO_2$ particles (anatase) having an average diameter of 0.31 $\mu$m (Instituto Guido Donegani Montedison Group, Novara, Italy, name P112F) are suspended in 1 l of fully deionized water. The suspension is heated to 75° C., and the pH is brought to 4. An $FeCl_3$ solution (80 g of $FeCl_3$/l of $H_2O$) is added at a metering rate of 2.0 ml/min, while maintaining the pH constant by simultaneously metering in a 15% aqueous NaOH solution. The coating is stopped as soon as a red-violet color has been reached; the iron oxide weight proportion is 394%. The coated pigment is separated off, washed and dried at 120° C. The pigment is then ignited at 900° C. for ½ h. The ignited pigment has a red-violet color and is distinguished by a very high covering power.

Example 2

10 g of finely powdered $TiO_2$ (Instituto Guido Donegani Montedison Group, Novara, Italy, name P112F) are suspended in 2 l of fully deionized water. The pH is brought to 4.0 with 2.5% aqueous hydrochloric acid, and the suspension is heated to 75° C. 3.3 l of an aqueous 0.5 molar $FeCl_3$ solution are then metered into the suspension over a period of 15.7 hours. During the addition of the $FeCl_3$ solution, the pH is maintained at 9.0 using 15% aqueous NaOH. After the addition of $FeCl_3$ solution is complete, the pigment has a red-violet color the iron oxide weight proportion is 1300%. Stirring of the mixture at 75° C. is continued for 15 minutes. The reaction suspension is then allowed to cool, filtered off, and the product is washed with fully deionized water until free of $Cl^-$. The pigment is then dried at 110° C. overnight and ignited at 800° C. for 30 minutes. The average particle size is 2.78 $\mu$m and the particle size distribution is narrow: 50% of the particles have a diameter of less than 2.8 $\mu$m and 90% of the particles have a diameter of less than 5.14 $\mu$m.

Example 3

5 g of finely powdered $TiO_2$ (Instituto Guido Donegani Montedison Group, Novara, Italy, name P112F) are suspended in 1 l of fully deionized water. The pH is brought to 4.0 with 2.5% aqueous hydrochloric acid, and the suspension is heated to 75° C. 4.1 l of an aqueous 0.5 molar $FeCl_3$ solution are then metered into the suspension over a period of 19 hours. During the addition of the $FeCl_3$ solution, the pH is maintained at 9.0 using 15% aqueous NaOH. After the addition of $FeCl_3$ solution is complete, the pigment has a black-violet color the iron oxide weight proportion is 2003%. Stirring of the mixture at 75° C. is continued for 15 minutes. The reaction suspension is then allowed to cool, filtered off, and the product is washed with fully deionized water until free of $Cl^-$. The pigment is then dried at 110° C. overnight and ignited at 800° C. for 30 minutes.

Example 4

A pigment prepared according to Example 3 is ignited at 900° C. for 30 minutes. This gives a black pigment.

Example 5

A paint formulation containing 3 g of a pigment prepared according to Example 1 and having an iron oxide weight proportion of 413%, 4 g of the silvery white [pearl luster] pigment Iriodin$^R$ 9103 (commercial product from E. Merck, Darmstadt), 93 g of the colorless basepaint from Herberts and 30 g of the dilution from Herberts shows a distinct color flop when drawn down.

Example 6

A paint formulation containing 6 g of a pigment prepared according to Example 1 and having an iron oxide weight proportion of 413%, 12.5 g of an 8% aluminium paste, 81.5 g of the colorless base paint from Herberts and 30 g of the dilution from Herberts shows a distinct color flop when drawn down.

The preceding examples can be repeated with similar success by substituting the generically or specifically described reactants and/or operating conditions of this invention for those used in the preceding examples.

From the foregoing description, one skilled in the art can easily ascertain the essential characteristics of thie invention, and without departing from the spirit and scope thereof, can make various changes and modifications of the invention to adapt it to various usages and conditions.

We claim:

1. A pigment comprising a non platelet-shaped silica, zirconium dioxide and/or titanium dioxide particle substrate coated with iron oxide, wherein the iron oxide content is at least 350% by weight, relative to the weight of the substrate.

2. A pigment according to claim 1, wherein the silica, zirconium dioxide and/or titanium dioxide particle has a diameter of less than 5 μm.

3. A pigment according to claim 1, wherein the iron oxide is doped with one or more other metal oxides.

4. A pigment according to claim 1, wherein the iron oxide content is more than 500% by weight.

5. A pigment according to claim 1, wherein the iron content is more than 750% by weight.

6. A pigment according to claim 1, whereby the iron oxide is a non-magnetic, black iron oxide.

7. In a paint, plastic or cosmetic containing a pigment, the improvement wherein the pigment is the pigment of claim 1.

8. A process for the preparation of non platelet-shaped pigments comprising:
   a. providing a suspension of silica, zirconium dioxide and/or titanium dioxide substrate particles in water;
   b. preparing a solution of aqueous iron salts which may optionally contain other metal salts; and
   c. metering said solution into said suspension while the pH of the suspension is maintained at a level to effect the hydrolysis of the iron and said optional metal salts of the solution by simultaneous addition of a base, thereby coating said substrate particles with iron oxide such that the iron oxide content is at least 350% by weight relative to the weight of the substrate particles.

9. A pigment according to claim 1, wherein the substrate is spherical.

10. A pigment according to claim 1, wherein the substrate has an irregular 3-dimensional shape.

11. A pigment according to claim 1, wherein the substrate is a monodisperse particle.

12. A pigment according to claim 1, wherein the substrate has a particle diameter of about 0.08 to 0.9 μm.

13. A pigment according to claim 1, wherein the substrate has a particle diameter of about 0.1 to 0.75 μm.

14. A pigment according to claim 1, wherein the substrate has a particle diameter less than 2.5 μm.

15. A pigment according to claim 1, wherein the iron oxide content is more than 400% by weight.

16. The process of claim 8 wherein the coated particles are separated, washed, dried and calcined.

* * * * *